(12) United States Patent
Anselmi

(10) Patent No.: US 9,272,146 B2
(45) Date of Patent: Mar. 1, 2016

(54) IMPLANTABLE MEDICAL DEVICE WITH ACTIVE DETECTION OF ATRIAL MECHANICAL ACTIVITY

(71) Applicant: SORIN CRM S.A.S., Clamart (FR)

(72) Inventor: Francesca Anselmi, Clamart (FR)

(73) Assignee: SORIN CRM S.A.S., Clamart (FR)

( * ) Notice: Subject to any disclaimer, the term of this patent is extended or adjusted under 35 U.S.C. 154(b) by 48 days.

(21) Appl. No.: 14/092,574

(22) Filed: Nov. 27, 2013

(65) Prior Publication Data

US 2014/0148713 A1    May 29, 2014

(30) Foreign Application Priority Data

Nov. 29, 2012 (FR) ...................................... 12 61424

(51) Int. Cl.

| A61B 5/02 | (2006.01) |
|---|---|
| A61N 1/365 | (2006.01) |
| A61B 5/024 | (2006.01) |
| A61N 1/362 | (2006.01) |
| A61N 1/368 | (2006.01) |
| A61N 1/37 | (2006.01) |

(52) U.S. Cl.
CPC ............ *A61N 1/36578* (2013.01); *A61B 5/024* (2013.01); *A61N 1/3624* (2013.01); *A61N 1/3682* (2013.01); *A61N 1/3704* (2013.01)

(58) Field of Classification Search
CPC .................... A61N 1/36578; A61B 2562/0219
USPC ................................ 600/508–528; 607/1–28
See application file for complete search history.

(56) References Cited

U.S. PATENT DOCUMENTS

| 2004/0172079 A1* | 9/2004 | Chinchoy ........................ 607/17 |
| 2006/0293715 A1* | 12/2006 | Plicchi et al. ...................... 607/9 |
| 2007/0179542 A1* | 8/2007 | Prakash et al. ..................... 607/9 |

FOREIGN PATENT DOCUMENTS

| EP | 0 515 319 | 11/1992 |
| EP | 2 092 885 A1 | 8/2009 |
| EP | 2 189 180 | 5/2010 |
| EP | 2 471 575 | 7/2012 |

OTHER PUBLICATIONS

Preliminary Search Report for French Patent Application No. 1261424, dated Jul. 3, 2013, 2 pages.

* cited by examiner

*Primary Examiner* — Amanda Patton
*Assistant Examiner* — Philip Edwards
(74) *Attorney, Agent, or Firm* — Foley & Lardner LLP

(57) ABSTRACT

A device includes a lead configured to for use in applying an atrioventricular delay ("AVD"), an acceleration sensor adapted to output an endocardial acceleration signal, and circuitry configured to receive and process said endocardial acceleration signal to provide ventricular pacing by varying, in a controlled manner, the AVD in a range having a plurality of AVD values. The circuitry derives from said endocardial acceleration signal a value of a parameter representative of an component of the endocardial acceleration signal corresponding to the first endocardial acceleration peak associated with an isovolumetric ventricular contraction ("EAX component"), and evaluates a degree of variation of said parameter values as a function of said plurality of AVD values to detect atrial and ventricular events.

12 Claims, 5 Drawing Sheets

IMPLANTABLE MEDICAL DEVICE WITH ACTIVE DETECTION OF ATRIAL MECHANICAL ACTIVITY

CROSS-REFERENCE TO RELATED APPLICATION

This application claims the benefit of and priority to French Patent Application No. 1261424, filed Nov. 29, 2012, which is incorporated herein by reference in its entirety.

BACKGROUND

The device relates to "active implantable medical devices" as defined by the Directive 90/385/EEC of 20 Jun. 1990 the Council of the European Communities. More specifically, the device relates to implants to continuously monitor heart rhythm and which are capable of delivering to the heart electrical pulses for stimulation, resynchronization and/or defibrillation in case of arrhythmia detected by the device.

The device also relates to the diagnosis of atrial contraction disorders. These disorders usually appear as aftermath of an episode of atrial fibrillation (AF). Atrial fibrillation is an arrhythmia characterized by abnormally high frequency of the atrial rhythm. Atrial contraction disorders may also result from other conditions such as atrial ischemia or dilated atrium by sarcoidosis or fibrosis. After an episode of AF, the contraction of the myocardium at the atrium is deficient or absent, despite the presence of a spontaneous or stimulated observable electric depolarization wave. An atonic atrium muscle leads to a lower contribution from the atrium muscle to fill the ventricle. This results in a very marked deterioration in hemodynamic performance. In such a situation, it may not be possible to optimize a double chamber operation of a device with atrial and ventricular sensing and ventricular stimulation. In this mode, the device triggers when ventricular pacing may be required or desirable after a predetermined atrioventricular delay (AVD). The AVD is counted from the detection of a spontaneous or paced atrial event. This AVD is normally adjusted to optimize the overall functioning of the heart from the hemodynamic point of view. In the case of atrial atony, the normal electrical activity causes the application of the AVD. However, it is challenging to optimize this delay because the actual behavior of the atrium is not known.

With the exception of an exploration by echocardiography, it is challenging to determine whether, after an episode of AF, a patient has recovered to normal mechanical atrial activity. It is also challenging to determine when that recovery has occurred. Furthermore, it is challenging to determine if there is an atrial atony, an absent or deficient contraction of the atrium despite an observable electrical activity (sinus rhythm).

SUMMARY

One embodiment of the device relates to evaluating the mechanical activity of the atrium, especially the return to normal atrial activity after an episode of AF. The device may also be capable of diagnosing the presence of atrial atony.

In one embodiment of the invention, the device evaluates the mechanical activity of the atrium by measuring an endocardial acceleration signal (EA). EA is a parameter of a component related to the mechanical activity of the ventricle and related to the modulation of the AVD. If the result of this modulation is a significant variation of the parameter in question, then this reflects the correct mechanical activity of the atrium. Conversely, the absence of significant change in the parameter may indicate an absent of or degraded atrial activity. With such an analysis, an implantable device can automatically establish the state of the atrial activity of the patient. Further, the implantable device, using this analysis, can determine when the patient has regained normal mechanical atrial activity after an episode of AF. Moreover, in the absence of proven atrial mechanical activity, it is possible to disable algorithms which would be ineffective in the absence of such activity. For example, AVD automatic optimization algorithms can be disabled.

U.S. 2007/0179542 A1 describes a device including methods of adjustment of the AVD allowing dynamic optimization of the patient's hemodynamic status. The device is further capable of detecting the presence or absence of atrial fibrillation, an atrial tachycardia episode or other pathological episodes of the same nature of the atrium. The device may also inhibit the adjustment of the AVD during the duration of such a proven episode. An adjustment calculation made during an episode would be strongly biased by the patient's medical condition and could result in deleterious effects in the patient.

In some embodiments, the device disclosed herein may not take action according to the presence or absence of an episode of atrial fibrillation. The device, once the fibrillation has ended, assesses the quality (i.e., normal, toneless or virtually absent) of the atrial contraction in sinus rhythm, i.e. the quality of the mechanical activity of the atrium when the latter has an observable electrical activity.

To this end, some embodiments of the device include an active implantable medical device such as a cardiac prosthetic for pacing, resynchronization and/or defibrillation. Some embodiments include a detector for detecting atrial and ventricular events. Some embodiments include a pacer for ventricular pacing. Also included may be methods for applying an atrioventricular delay AVD, counted from the detection of a spontaneous or stimulated atrial event and after which a ventricular stimulation is delivered in the absence of detection of a corresponding spontaneous ventricular event, to the stimulation methods. Some embodiments also include an acceleration sensor adapted to output an endocardial acceleration signal (EA) representative of the movements produced by the cyclical contractions of the myocardium. Some embodiments of the device include methods to analyze the EA signal. These methods derive, from the EA signal, a value EA of a representative non-temporal EA ventricular parameter of a component EA1 of the signal corresponding to the first peak EA associated with the isovolumetric ventricular contraction. Further included within some embodiments of the device are scanning methods, capable of varying in a controlled manner the AVD. The AVD is varied in a range having a plurality of AVD values. Some embodiments also include a quantifier, for evaluating a degree of variation of the ventricular EA parameter corresponding to a plurality of values of the AVD.

In addition to the features disclosed in U.S. 2007/0179542 A1, some embodiments of the device, further include a detector which is capable of discriminating between: i) a normal atrial mechanical activity, and ii) an absent or deficient atrial mechanical activity despite an observable electrical activity in sinus rhythm. The embodiment discriminates as a function of the degree of variation in the non-temporal ventricular EA parameter estimated by the quantifier described above.

The non-temporal ventricular EA parameter can notably be the peak-to-peak amplitude of the EA signal of the EA1 component. The non-temporal ventricular EA parameter may also be the energy of the EA1 component.

In a first embodiment of the device, there is a range of values of the AVD including a first range with a plurality of short AVD and a second range with a plurality of long AVD. The second range of AVD values is distinct from the first one. The quantifier assess the degree of variation in the non-temporal ventricular EA parameter by computing a difference between the values of the EA ventricular parameter collected for the first range of AVD values and the values of the EA ventricular parameter collected for the second range of AVD values. The detector discriminates between a normal atrial mechanical activity and an absent or deficient atrial mechanical activity. When the difference between the EA ventricular parameters for different AVD values exceeds a predetermined threshold, there is normal atrial activity. When the threshold is not exceeded, the atrial activity is absent or deficient.

In a second embodiment of the device, the quantifier is adapted to evaluate the degree of variation in the EA ventricular parameter by computing a standard deviation of the EA ventricular parameter values collected for the various AVD of said range of values. The detector, capable of detecting atrial activity, is able to discriminate between a normal atrial mechanical activity and an absent or deficient atrial mechanical activity. When the standard deviation exceeds a predetermined threshold, the atrial mechanical activity is normal. When the standard deviation calculated by the quantifier does not exceed the predetermined threshold, there is absent or deficient atrial mechanical activity.

In a third embodiment of the device, the quantifier is adapted to evaluate the degree of variation by modeling the sigmoid characteristic of variation in the EA ventricular parameter as a function of AVD range values, with two plateaus on either side of a central transition portion. The detector, for detecting atrial activity, is able to discriminate between a normal atrial mechanical activity when the absolute difference in the level of the two plateaus is larger than a predetermined threshold. An absent or deficient atrial mechanical activity is detected when absolute difference of the two plateaus is less than the predetermined threshold.

In some embodiments of the device, the techniques described above may be used to store an index function of the degree of variation of the EA ventricular parameter as a function of the plurality of AVD values. Additionally, the index function may be used to form a history of the evolution of the index over time.

In embodiments where the device further includes a stimulation device, for atrial stimulation, it is possible for the embodiment to implement a detector for detecting atrial activity in the presence of a spontaneous atrial event. The detector may detect atrial activity related to an atrial paced event. The detector may compare the respective stored values of the index and derive from this comparison a warning indicator in case of discrepancy with the respective compared index. In the case of an episode of atrial fibrillation, it is possible to compare the stored values of that index, prior to and after the episode of atrial fibrillation, and derive from this comparison an indicator of recovery or no recovery from the atrial fibrillation.

DETAILED DESCRIPTION

An exemplary embodiment of the device is illustrated with reference to the accompanying drawings as described below.

Aspects of the device may be applied to implantable devices such as the Paradym family (especially Paradym RF SonR CRT-D) produced and marketed by Sorin CRM, Clamart, France.

These are programmable microprocessor devices including circuitry to receive, format and process electrical signals collected by implanted electrodes. These devices also deliver stimulation pulses to electrodes. It is possible, using telemetry software that is stored in memory and is executed, to implement some of the features of the device that are described below (parameter optimization and monitoring of the patient's status). The adaptation of these devices for the implementation of the functions of some of the embodiments of the device is within the skill in the art and is not described in detail.

The technique used in some embodiments of the device is based on the analysis of the endocardial acceleration (hereinafter "EA"). EA is a parameter that reflects very precisely, and in real time, phenomena contributing to the mechanical operation of the myocardium. EA may be measured by an accelerometer coupled to the heart muscle. This technique is described, for example, in EP 0515319 A1 (Sorin Biomedica Cardio SpA). This document discloses the method to collect an EA signal through an endocardial lead with a stimulation distal electrode implanted in the atrium or in the ventricle. A microaccelerometer is included for measuring endocardial acceleration.

Such a sensor as a the one described in EP 0515319 A1 or another microaccelerometer may be arranged on an endocardial lead terminating at the apex of the ventricle. An acceleration sensor is provided at that location. The sensor may also be a lead provided with an acceleration sensor at its one end disposed against the wall of the right atrium. Note that although the present description refers mainly to the analysis of an EA signal delivered by a sensor on an endocardial lead, some embodiments of the device may perform an analysis using an EA signal delivered by other types of implantable sensors. For example, these implantable sensors may include a motion sensor of a wall of the myocardium, an epicardial sensor, or an accelerometer in the housing of an implant.

Some embodiments of the device are also applicable of performing the analysis using an external EA signal obtained non-invasively. For example, a sensor may be attached to the patient's chest at the sternum.

Figure 1:
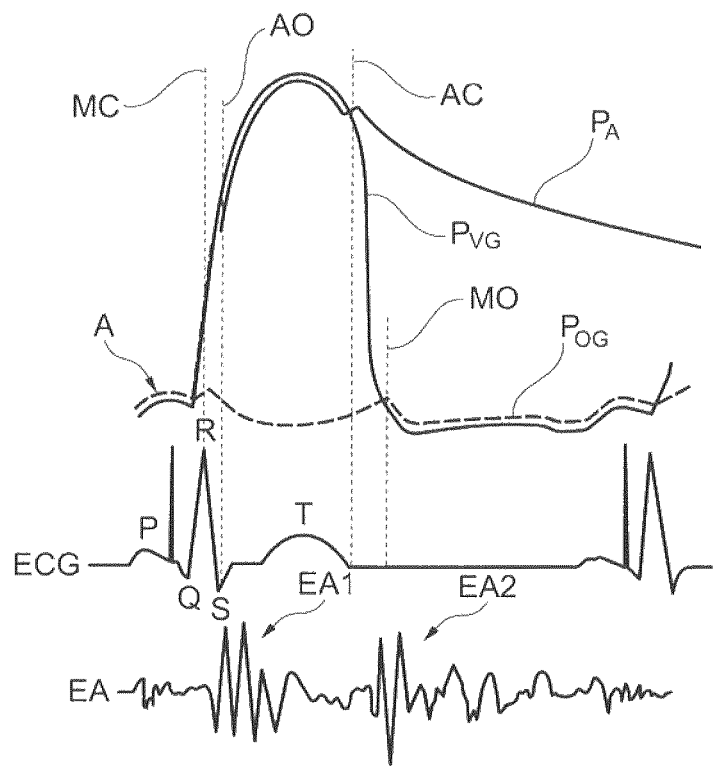
FIG. 1 is a series of graphs illustrating three different characteristic signals that can be collected during a cardiac cycle.

FIG. 1 illustrates the various signals characterizing the activity of the heart during a cardiac cycle. The profiles of intracardiac pressures $P_A$, $P_{VG}$ and $P_{OG}$ are shown. The $P_A$ profile shows the changes in the aortic pressure. The $P_{VG}$ profile shows changes in the left ventricular pressure. The $P_{OG}$ profile shows changes in the left atrium pressure. These changes go through phases including: a contraction of the left atrium, closure of the mitral valve (MC), opening of the aortic valve (AO), closure of the aortic valve (AC), and opening of the mitral valve (MO). An ECG surface electrocardiogram plot is also shown corresponding to the same period of time. The ECG surface electrocardiogram plot includes the P wave corresponding to the depolarization of the atria, the QRS complex corresponding to the depolarization of the ventricles, and the T wave of ventricular repolarization. Also shown are the changes in the collected EA endocardial acceleration signal. The EA endocarial acceleration signal forms two main components EA1 and EA2 during a given cardiac cycle. The two main components correspond to the two major heart sounds (S1 and S2 sounds of the phonocardiogram) that can be recognized in each cardiac cycle.

Figure 2:
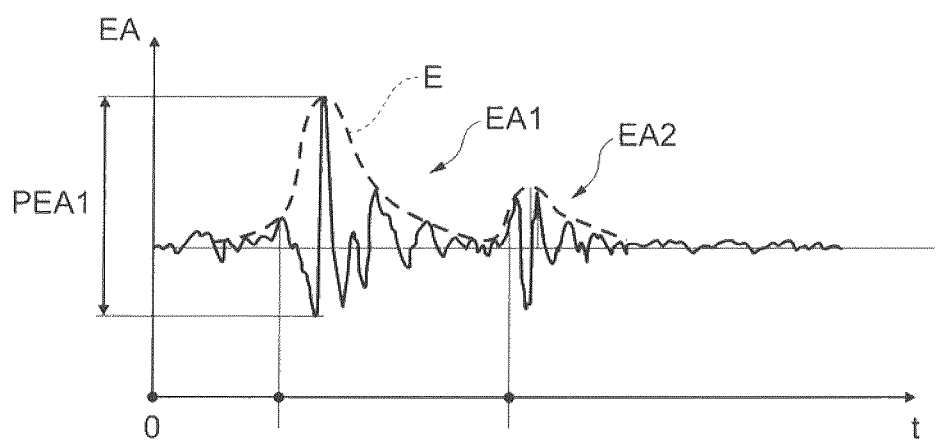
FIG. 2 shows in more detail the shape of the endocardial acceleration signal during a given cycle.

In FIG. 2, changes in the EA signal during a cardiac cycle are more specifically illustrated. The EA1 component begins after the QRS complex and is caused by a combination of the closing of the atrioventricular valves (the mitral and the tricuspid valves), the opening of semilunar valves (the aortic and the pulmonary valves), and the contraction of the left ventricle. The amplitude variations of this EA1 component are closely related to changes in the pressure in the ventricle. The maximum peak-to-peak PEA1 is specifically correlated to the positive maximum of the pressure variation dP/dt in the left ventricle. The EA2 component occurs during the isovolumetric ventricular relaxation phase. It supports the end of the ventricular systole and is mainly produced by the closure of the aortic and pulmonary valves.

For the implementation of some embodiments of the device, the device may extract from the EA signal, specifically from the EA1 component, a non-temporal parameter characteristic of the magnitude of this EA1 component. This parameter can particularly be the PEA1 amplitude of the first peak of endocardial acceleration. PEA1 amplitude is the maximum peak-to-peak value between the positive and negative extremes of the EA1 component of the acceleration signal. This PEA1 parameter is used in the following description as a significant non-temporal parameter. In some embodiments, other parameters representative of the magnitude of EA1 component may be used.

In particular, it is possible to use as a significant non-temporal parameter the energy of the EA signal contained in all or part of the EA1 component. This energy is given by the root mean square (RMS) value of a series of samples considered for a predetermined time window of the EA1 component. This energy parameter is illustrated in FIG. 2 by the envelope E of the signal.

The analysis of the EA signal is preferably determined with averaging over several cycles, typically three to five cycles, using a technique such as that disclosed in EP 2092885 A1 (ELA Medical). This technique is useful for eliminating the cycle to cycle variations by a timing shift of the successive components before averaging.

Essentially, this technique is to pre-process the continuously collected EA signal. The EA signal is cut into sub-signals each corresponding to the duration of a cardiac cycle and identified by cycle start markers (time origin) for performing this cutting cycle. The cycle start temporal markers can be provided by the implanted device. The device also, according to the operating mode, stores the moments of V stimulation or the moments of R wave detection. Each of these sub-signals is segmented so as to individualize the EA1 component in a given temporal window. For the current EA1 component thus isolated on a cycle, an inter-correlation peak relative to the EA1 components of the other collected cycles is determined. A corresponding temporal shift is computed. The calculated temporal shift is applied to the current EA1 component so as to align it with respect to the others. The analysis processing of the EA signal can then be executed on successive EA1 components, eliminating cycle to cycle variability bias through this pre-processing.

In some embodiments of the device, atrioventricular delay (AVD) is modulated. The changes to the non-temporal characteristic parameter of the EA signal, in this example the PEA1 amplitude, are produced by this modulation of the AVD.

Figure 3A:
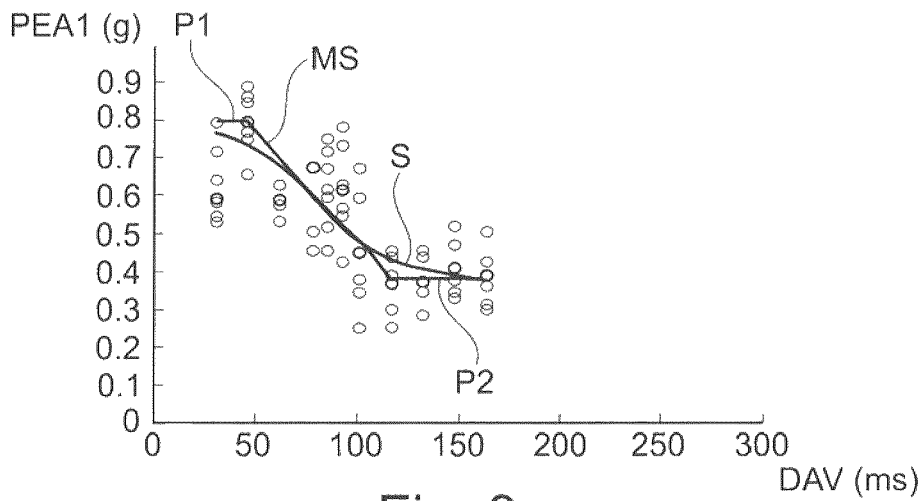
FIGS. 3a-3c show the classic form of a variation of the amplitude of the first peak of the EA signal versus the AVD characteristic for a healthy subject (FIG. 3a) and with the changes that this characteristic may present in case of an absence of atrial mechanical activity (FIG. 3b) or in case of atrial atony (FIG. 3c).

The variation of the PEA1 amplitude with the AVD is normally associated with a sigmoid shape characteristic S, shown in FIG. 3a. In this figure and the following ones, the thin line circles indicate the different readings in successive cardiac cycles for the same applied AVD value. The thick line circles correspond to the value of these different measures averaged for a same AVD.

The PEA1 amplitude decreases when the AVD increases, and the sigmoid characteristic can be modeled in a simplified form MS with two plateaus P1, P2 respectively corresponding to the short AVD and to the long AVD, these plateaus being separated by a central transition portion with a negative slope.

Some embodiments of the device are based on the idea that changes in the EA1 characteristic versus the AVD, such as changes in the PEA1 amplitude, are due, among other factors, to the different contribution of the atrium for the filling of the ventricle. A short AVD maximizes the filling of the ventricle, leading to a very marked EA peak signal. A long AVD reduces the amplitude and the energy of the EA1 component.

Figure 3B:
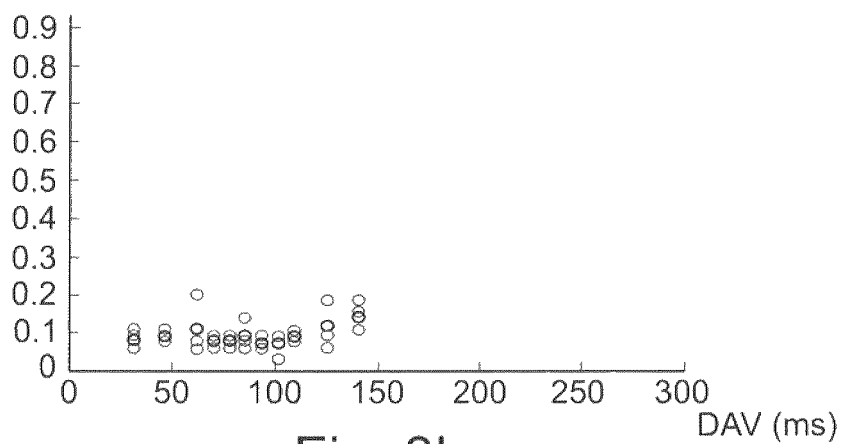

When the atrial mechanical activity is absent, typically after an episode of atrial fibrillation (AF), the atrium may fail to contribute in any way to fill the ventricle. A variation of the AVD produces no significant change in the EA1 component. This situation is illustrated in FIG. 3b. The level of the PEA1 amplitude is essentially the same regardless of the applied, short or long, AVD.

Figure 3C:
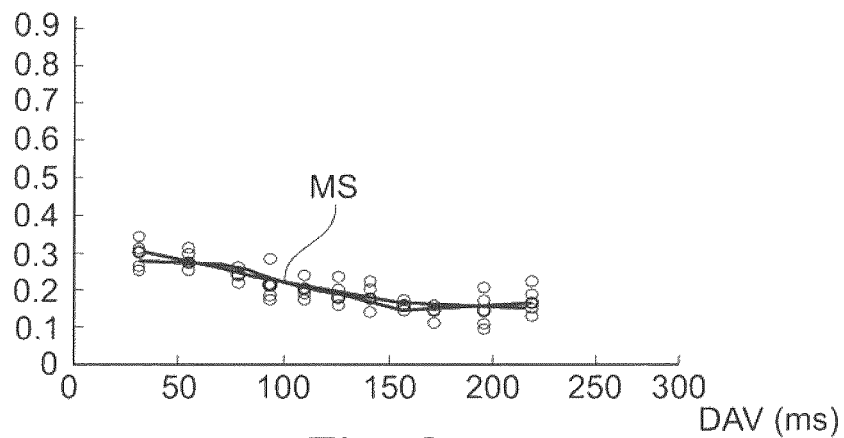

In the case of a present but deficient atrial contraction (atrial atony), the PEA1 amplitude varies slightly with the AVD (shown FIG. 3c status). The variation of the PEA1 amplitude with respect to AVD is much less than in the case of a full atrial contraction (FIG. 3a).

Figure 4A:
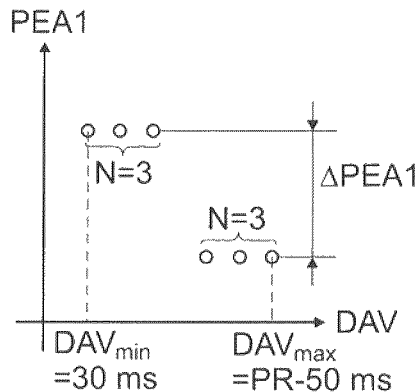
FIGS. 4a and 4b illustrate a first technique for analyzing the characteristic of FIG. 3a to discriminate between normal and abnormal or absent atrial activity.
Figure 4B:
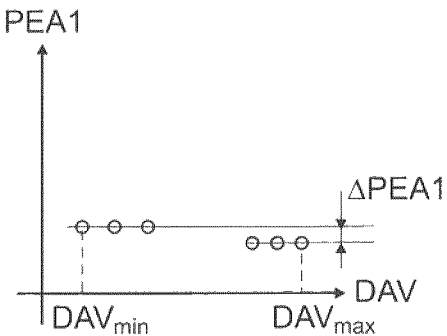

Different techniques can be used to analyze the PEA1/AVD characteristic and discriminate between normal atrial activity and absent or deficient atrial activity. Some embodiments may include a first technique, alone or in conjunction with other techniques. The first technique is illustrated with reference to FIGS. 4a and 4b. A number N of short test AVD values are applied. Separately, a number N of long test AVD values are applied. The PEA1 amplitude is measured for each of these applied AVD values.

The test AVD are selected from a bounded range of values. For example, some embodiments may use minimum values $DAV_{min}$=32 ms for the shortest value and maximum $DAV_{max}$=PR-50 ms for the longest AVD. PR is the interval between the atrial and ventricular depolarizations and 50 ms corresponds to a predetermined safety margin in this example. In some embodiments, the number N, which defines the number of long and short AVD to test, can be for example between 3 and 20. The different tested AVD are performed with a fixed pitch, for example 15 ms between two consecutive AVD.

For each tested AVD, the PEA1 amplitude is measured and averaged over a number of cycles. For example, some embodiments may take measurements for six or more cardiac cycles.

To determine the level of atrial activity, a difference is calculated between the average values of PEA1 measured for the N short AVD, and the average values of PEA1 measured for the N long AVD. If this absolute difference is less than a programmable threshold, there is an absence of normal mechanical atrial activity (as in FIG. 4b). In other words, there is absent or deficient atrial activity. If the absolute difference is greater than the programmable threshold, there is normal mechanical atrial activity. In some embodiments, the value of the calculated difference is preferably stored in memory. The stored values may constitute a history that may be used to monitor the long-term atrial mechanical activity. This is explained below with reference to FIGS. 7 and 8.

Figure 5A:
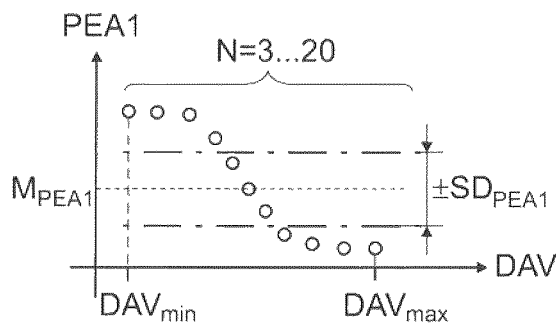
FIGS. 5a and 5b are counterparts of the previous figures illustrating a second analysis technique.
Figure 5B:
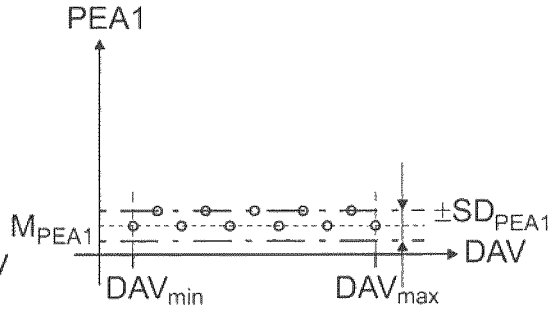

Some embodiments may use a second technique, alone or in conjunction with other techniques, to analyze the PEA1/AVD characteristic and discriminate between normal atrial activity and absent or deficient atrial activity. This second technique is illustrated with reference to FIGS. 5a and 5b. The AVD is regularly modulated with a scan between the $DAV_{min}$ and $DAV_{max}$ values. This can be done to obtain a number N of successive measurements of equidistant AVD values. In some embodiments, N may typically be between 4 and 20. For each tested AVD, the PEA1 amplitude is measured and averaged over several cycles. In some embodiments, the PEA1 amplitude is measured for typically at least six cardiac cycles.

The standard deviation $SD_{PEA1}$ is then calculated from all the averaged values of PEA1. If the standard deviation is below a given threshold, then there is no normal mechanical atrial activity (as in FIG. 5b). There is absent or deficient atrial activity. If the standard deviation $SD_{PEA1}$ is greater than the given threshold, there is normal mechanical atrial activity. In some embodiments, the value of the calculated standard deviation may be stored in memory to monitor the long-term atrial mechanical activity of the patient.

Figure 6A:
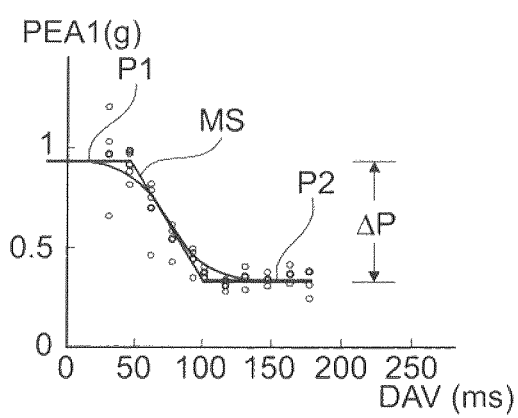
FIGS. 6a and 6b are counterparts of the previous figures illustrating a third analysis technique.
Figure 6B:
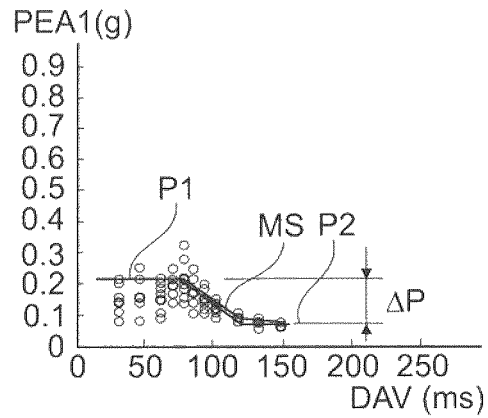

Some embodiments may use a third technique, alone or in conjunction with other techniques, to analyze the PEA1/AVD characteristic and discriminate between normal atrial activity and absent or deficient atrial activity. The third technique is illustrated with reference to FIGS. 6a and 6b. The third technique is a variant of the second technique described above. This technique operates by creating a MS model of the PEA1 characteristic obtained after scanning the range of possible AVD between $DAV_{min}$ and $DAV_{max}$.

As noted above, the modeled characteristic has two plateaus, P1 for the lowest AVD values and P2 for the highest AVD values. This is typical of a sigmoid shape. The atrial activity is estimated by calculating the absolute difference ΔP between the two plateaus P1 and P2 of the sigmoid approximation. If this difference is less than a given threshold, then there is an absence of normal atrial mechanical activity (as in FIG. 6b). In other words, there is absent or deficient atrial activity. If the difference is greater than the given threshold, there is normal mechanical atrial activity.

Figure 7:
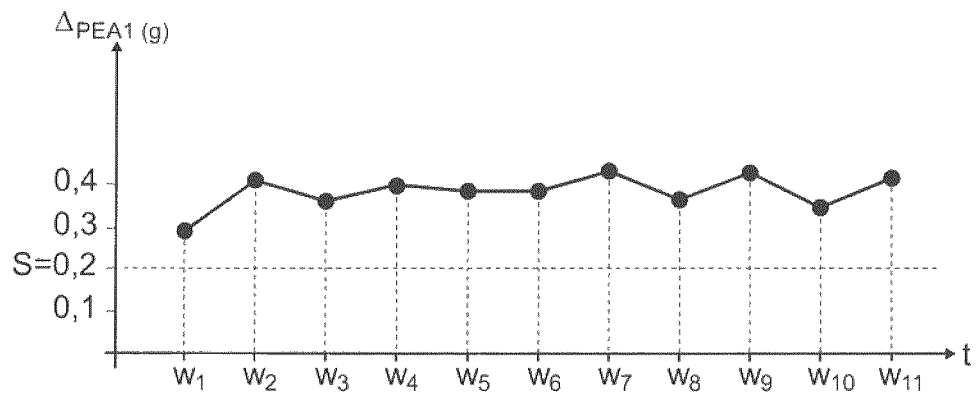
FIG. 7 illustrates, according to one embodiment, the manner of monitoring, over several weeks, the atrial activity in the case wherein it is considered normal.
Figure 8:
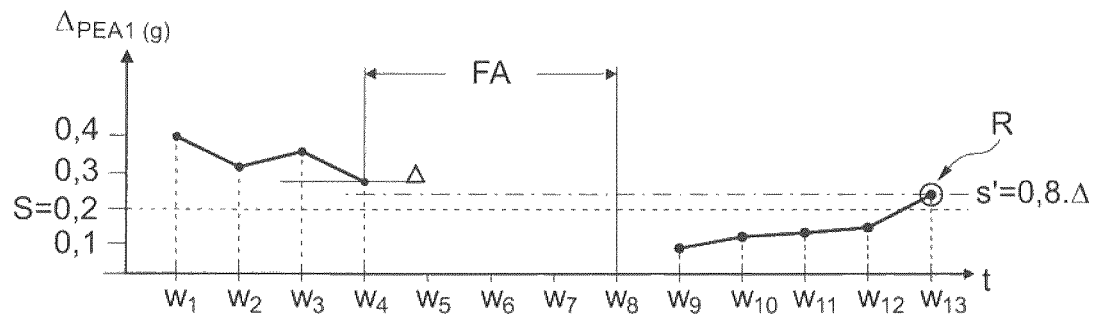
FIG. 8 is a counterpart of FIG. 7 illustrating, according to one embodiment, the case of an episode of atrial fibrillation lasting for several weeks, in which a deficient mechanical atrial activity is monitored until the activity can be considered as returned to normal.
Figure 9:
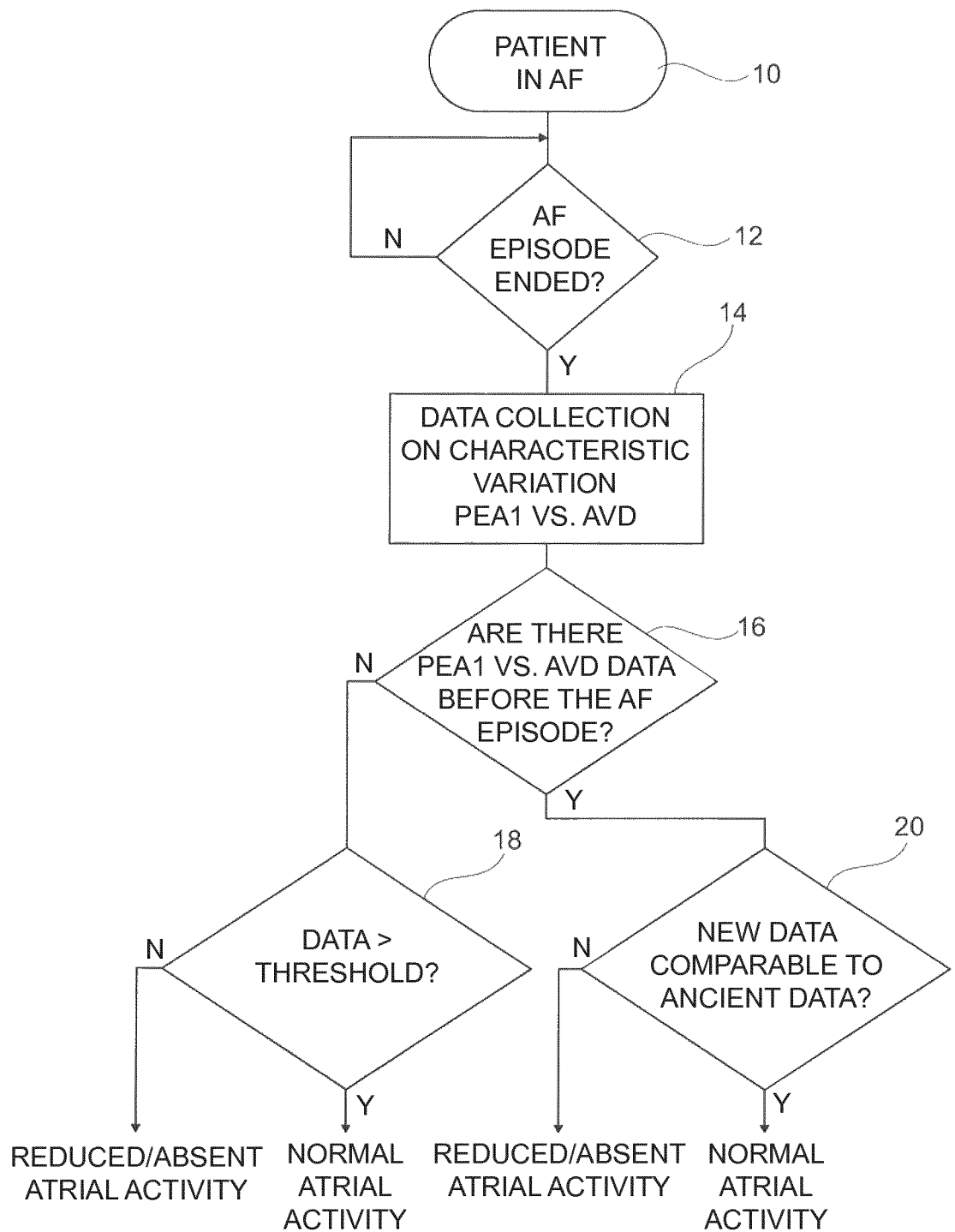
FIG. 9 is a flowchart schematically describing the sequence over time of the different steps of monitoring and diagnosis of the atrial activity according to one embodiment.

FIGS. 7 and 8 and the flow chart of FIG. 9 illustrate the possibility of using the atrial mechanical activity test techniques described above to monitor the patient's long-term clinical status. In some embodiments, a test can be triggered periodically. For example, the test may occur weekly or more frequently to determine the status of the atrial activity. This test may be run for both spontaneous and stimulated atrial depolarization. In the case of stimulated atrial activity, the test may occur in conditions in which atrial capture is likely. To facilitate atrial capture, stimulation amplitude is adjusted at a high level during the test. In some embodiments, stimulation amplitude is previously checked for the presence of an actual atrial capture.

For testing, the AVD is modulated in order to evaluate a degree of variation of the EA1 characteristic versus the AVD according to one of the techniques described above. For example, the difference $\Delta_{PEA1}$ calculated between the PEA1 amplitude collected for the short AVD and those collected for the long AVD may be stored. This corresponds with the first technique for discriminating between normal atrial activity and absent or deficient atrial activity described above. Some embodiments may use a different combination of one or more of the techniques described. If this $\Delta_{PEA1}$ value is greater than a given threshold S, atrial activity is present and normal. If the $\Delta_{PEA1}$ value is less than a given threshold, atrial activity is absent or deficient (atrial atony). In some embodiments, the device compares the respective values of the $\Delta_{PEA1}$ stored value in the presence of a spontaneous atrial event and in the presence of an atrial paced event. The device may generate an alert in the case of a discrepancy between the compared values.

FIG. 7 shows an example in which the $\Delta_{PEA1}$ value is evaluated at weekly intervals (W1, W2, W3, . . . ). The $\Delta_{PEA1}$ value corresponding to each week is stored. These stored values may be used to form a long-term history of global atrial mechanical activity of the patient. FIG. 7 illustrates a normal atrial mechanical activity history. S is a threshold value against which the $\Delta_{PEA1}$ value for each week is compared. Each week shows normal atrial mechanical activity as the $\Delta_{PEA1}$ value is above the threshold value S. In a case where the $\Delta_{PEA1}$ value is below the threshold value S, atrial activity is absent or deficient (atrial atony).

FIG. 8 shows an example of an episode of atrial fibrillation AF leaving deficient mechanical atrial activity for several weeks. The end of this episode (between periods W4 and W8) can be detected by a return of sinus rhythm. The test for mechanical atrial activity is then performed using one of or a combination of the techniques described above. In the example illustrated by FIG. 8, the test indicates that during the periods W9 to W12 there was deficient atrial activity. The degree of PEA1/AVD variation is less than the threshold S. The patient has regained normal atrial activity when $\Delta_{PEA1}$ rises above this threshold. For example, the threshold may be S'=80% of the Δ value recorded by the $\Delta_{PEA1}$ variation parameter prior to the AF episode.

FIG. 9 illustrates a schematic of the successive steps of an algorithm to discriminate between the various possible states of atrial mechanical activity after an episode of atrial fibrillation. For a patient with atrial fibrillation (block 10), the device waits for the end of this episode (block 12). The end of the episode is detected by the return to a normal and stable sinus rhythm. The return to a normal and stable sinus rhythm may be determined by the analysis of the electrical activity of the depolarization signals detected at the atrium.

The device may then perform a test to assess the degree of variation of the PEA1 amplitude versus the AVD (block 14). The resulting test data is collected and stored. If test results were obtained and stored before the AF episode (block 16), then the algorithm compares the new data to the old data (block 20). If the data values are comparable (for example, if the $\Delta_{PEA1}$ variation parameter is at least 80% of the value it had before the episode of AF), the atrial activity returned to normal. If the test data values are not comparable to the values stored before the AF episode, the atrial activity is insufficient or absent.

If there is no data prior to the AF episode, the algorithm simply compares the test data to a threshold (block 18). If the test data values are greater than the threshold, there is normal mechanical atrial activity. If the test data values are less than the threshold, there is reduced or absent atrial activity. In some embodiments, the algorithm may use a combination of one or more of the techniques for discriminating between normal and absent or deficient atrial activity described above.

In some embodiments, the analysis of the atrial mechanical activity may also be used to selectively enable or disable various algorithms. These algorithms may include atrial overdriving, automatic optimization of the AVD, etc., depending on the test result.

For example, if atrial fibrillation is detected, using the analysis previously described herein, then the AVD algorithm may be disabled. Continued use of the AVD algorithm during atrial fibrillation may have deleterious effects. These effects may be prevented by the disabling of the AVD algorithm during episodes of atrial fibrillation detected by the device. In some embodiments, an atrial overdriving algorithm, designed to overdrive the atrium to prevent atrial fibrillation through a higher pacing rhythm, may be activated or enabled by the device. The device may enable this algorithm upon the detection of atrial fibrillation using the analysis previously described herein. In some embodiments, these algorithms may be disabled, enable, and/or modified depending on the detection of normal or deficient or absent atrial mechanical activity according to the analysis described herein. Furthermore, in some embodiments the device and/or analysis may automatically optimize the AVD using the techniques described herein (e.g. upon detection of absent or deficient atrial mechanical activity). In some embodiments, the device may produce an alert (e.g. signal, notification, data point, sound, visible signal, etc.) in certain cases. For example, the device may produce an alert when an algorithm is enabled, disabled, and/or modified. Continuing the example, the device may produce an alert upon the detection, using the analysis described herein, of absent or deficient atrial mechanical activity. The device may adjust a variable of an AVD algorithm. For example, the device may adjust one or more of the length of time of the AVD, the length of the time intervals between atrial sensing, the length of the time intervals between pacing, the number of cycles for which an extended or reduced AVD is applies, the value of and AVD extension, the value of an AVD reduction, the value of the AVD corresponding to different heart rates, the magnitude of the ventricular pacing stimulus, the rate adjustment value for exercise and other activities, the base pacing rate, etc. The AVD may be adjusted taking into account the optimal or desired interatrial conduction time, left-atrial electromechanical action, left-ventricular latency period, etc. The device may also adjust a variable of an atrial overdriving algorithm. For example the device may adjust one or more of rate of pacing, the frequency of stimulation, the magnitude of stimulation, the atrial rate, the rate adjustment value for exercise and other activities, the base pacing rate In one embodiment of the device, the device is not a pacing device. The device may be a monitor, server computer, personal computer, mobile device, clinic computer, or other device configured to apply the analysis techniques described. The device may also be configured to discriminate between normal and absent or deficient atrial mechanical activity and/or to determine if a patient is experiencing AF using the analysis techniques described above. In some embodiments, the device may be incorporated into another apparatus such as a patient bed, heart rate monitor, etc. Having received data such as the EA signal for a patient over time or a set of non-temporal EA ventricular parameter values over time (e.g. PEA1 amplitude or energy of the EA1 component of the EA signal), the device may perform the analysis techniques set forth above. The results of the analysis may be a determination of normal atrial mechanical activity or absent or deficient atrial mechanical activity. This determination may be over a period of time and/or live as data is received. For example, the device may display a graph such as the one illustrated in FIG. 7 or FIG. 8. The device may display a graph of the change of the non-temporal EA ventricular parameter values for different AVD values over time. The device may also label periods of normal atrial mechanical activity. The device may label periods of absent or deficient atrial mechanical activity. The device may also provide a current determination of whether a patient is experiencing AF. This determination may be based on the most recently available data. This determination may be presented to a user of the device through an alert. For example, the alert may be a visual warning (e.g. graphics or words which designate that the patient is experiencing AF), an auditory warning (e.g. an alarm when the patient is experiencing AF), or a warning otherwise delivered. In the case that the patient is not experiencing AF, a status indicator may be displayed to the user of the device. The analysis, analysis results, and/or warnings generated by the device may be displayed and/or delivered to a user. For example, the analysis and/or alerts may be displayed on a local monitor, remote monitor, emailed to a user, sent to a mobile device, pushed to an application on a mobile device, compiled into a report and printed, sent as a text message, sent as a page, broadcast over a public address system (e.g. in the case of an AF alert), displayed on a computer and/or monitor at a nurses station, stored locally, stored in a cloud based architecture, transferred to another computing device etc. In some embodiments, the device may compare analyzed data to a data in a stored index for a particular patient. This comparison and/or the resulting analysis may displayed in a manner described above.

The invention claimed is:
1. A device, comprising:
a lead having at least one electrode;
an acceleration sensor adapted to output an endocardial acceleration signal;
circuitry configured to receive and process said endocardial acceleration signal and to provide ventricular pacing using the lead by varying, in a controlled manner, an atrioventricular delay ("AVD") in a range having a plurality of AVD values,
wherein the circuitry derives from said endocardial acceleration signal a value of a parameter representative of a component of the endocardial acceleration signal corresponding to the first endocardial acceleration peak associated with an isovolumetric ventricular contraction ("EAX component"), and evaluates a degree of variation of said parameter values as a function of said plurality of AVD values to detect atrial and ventricular event;
wherein the circuitry is configured to evaluate said degree of variation of said parameter values as a function of said plurality of AVD values by calculating a difference between the values of the parameter collected for a first range of AVD values and the values of the parameter collected for a second range of AVD values, and wherein said first range of AVD values includes a plurality of short AVD values and said second range of AVD values, distinct from said first range of AVD values, includes a plurality of long AVD values; and wherein the circuitry is further configured to discriminate between a normal atrial mechanical activity, when said difference exceeds a predetermined threshold, and an absent or deficient atrial mechanical activity when said difference does not exceed said predetermined threshold.

2. The device of claim 1, wherein the AVD is counted from the detection of a spontaneous or stimulated atrial event and after which a ventricular stimulation is delivered in the absence of detection of a corresponding spontaneous ventricular event.

3. The device of claim 1, wherein the circuitry is configured to discriminate, as a function of said degree of variation of parameter values, between normal atrial mechanical activity and an absent or deficient atrial activity, despite an observable electrical activity in sinus rhythm.

4. The device of claim 1, wherein said parameter is the amplitude between extremes of the EAX component of the endocardial acceleration signal.

5. The device of claim 1, wherein said parameter is the energy of the EAX component of the endocardial acceleration signal.

6. The device of claim 1, wherein the circuitry is configured to evaluate said degree of variation of said parameter values as a function of said plurality of AVD values by calculating a standard deviation of the parameter values collected for said plurality of AVD values.

7. The device of claim 1, wherein the circuitry is configured to evaluate said degree of variation of said parameter values as a function of said plurality of AVD values by modeling a sigmoid characteristic of the parameter values as a function of said plurality of AVD values, with two plateaus, one on each side of a central transition portion.

8. The device of claim 1, further comprising memory configured to store an index of said degree of variation of the parameter values, wherein said memory is further configured to provide a history of the evolution of said index over time.

9. The device of claim 8, wherein the circuitry is configured to, upon the occurrence of an episode of atrial fibrillation (AF), compare the stored values of said index prior to the episode of atrial fibrillation (AF) and post the episode of atrial fibrillation (AF), and is configured to derive from this comparison a recovery indicator, or an indicator of an absence of recovery after atrial fibrillation (AF).

10. A device, comprising:
a lead having at least one electrode;
an acceleration sensor adapted to output an endocardial acceleration signal;
circuitry configured to receive and process said endocardial acceleration signal and to provide ventricular pacing using the lead by varying, in a controlled manner, an atrioventricular delay ("AVD") in a range having a plurality of AVD values,
wherein the circuitry derives from said endocardial acceleration signal a value of a parameter representative of a component of the endocardial acceleration signal corresponding to the first endocardial acceleration peak associated with an isovolumetric ventricular contraction ("EAX component"), and evaluates a degree of variation of said parameter values as a function of said plurality of AVD values to detect atrial and ventricular events;
wherein the circuitry is configured to evaluate said degree of variation of said parameter values as a function of said plurality of AVD values by calculating a standard deviation of the parameter values collected for said plurality of AVD values; and
wherein the circuitry is further configured to discriminate between a normal atrial mechanical activity, when said standard deviation exceeds a predetermined threshold, and an absent or deficient atrial mechanical activity when said standard deviation does not exceed said predetermined threshold.

11. A device, comprising:
a lead having at least one electrode;
an acceleration sensor adapted to output an endocardial acceleration signal;
circuitry configured to receive and process said endocardial acceleration signal and to provide ventricular pacing using the lead by varying, in a controlled manner, an atrioventricular delay ("AVD") in a range having a plurality of AVD values,
wherein the circuitry derives from said endocardial acceleration signal a value of a parameter representative of a component of the endocardial acceleration signal corresponding to the first endocardial acceleration peak associated with an isovolumetric ventricular contraction ("EAX component"), and evaluates a degree of variation of said parameter values as a function of said plurality of AVD values to detect atrial and ventricular events;
wherein the circuitry is configured to evaluate said degree of variation of said parameter values as a function of said plurality of AVD values by modeling a sigmoid characteristic of the parameter values as a function of said plurality of AVD values, with two plateaus, one on each side of a central transition portion; and
wherein the circuitry is further configured to discriminate between a normal atrial mechanical activity, when the absolute level difference of the two plateaus is larger than a predetermined threshold, and an absent or deficient atrial mechanical activity when the absolute level difference of the two plateaus is not larger than said predetermined threshold.

12. A device, comprising:
a lead having at least one electrode;
an acceleration sensor adapted to output an endocardial acceleration signal;
circuitry configured to receive and process said endocardial acceleration signal and to provide ventricular pacing using the lead by varying, in a controlled manner, an atrioventricular delay ("AVD") in a range having a plurality of AVD values,
wherein the circuitry derives from said endocardial acceleration signal a value of a parameter representative of a component of the endocardial acceleration signal corresponding to the first endocardial acceleration peak associated with an isovolumetric ventricular contraction ("EAX component"), and evaluates a degree of variation of said parameter values as a function of said plurality of AVD values to detect atrial and ventricular events;
memory configured to store an index of said degree of variation of the parameter values, wherein said memory is further configured to provide a history of the evolution of said index over time;
a stimulation device configured to provide atrial stimulation; and
wherein the circuitry is configured to provide an atrial paced event, and wherein the circuitry is configured to detect atrial activity in the presence of at least a spontaneous atrial event and at least an atrial paced event, and wherein the circuitry is configured to compare stored values of said index corresponding to the spontaneous atrial event with stored values of said index corresponding to the paced atrial event and to derive from this comparison a warning indicator in case of discrepancy between the respective compared indexes.

* * * * *